United States Patent [19]

Redmon

[11] Patent Number: 4,470,293

[45] Date of Patent: Sep. 11, 1984

[54] IMPACTING DEVICE FOR TESTING INSULATION

[75] Inventor: John W. Redmon, Huntsville, Ala.

[73] Assignee: The United States of America as represented by the Administrator of the National Aeronautics and Space Administration, Washington, D.C.

[21] Appl. No.: 460,509

[22] Filed: Jan. 24, 1983

[51] Int. Cl.³ .............................................. G01N 3/08
[52] U.S. Cl. .......................................... 73/12; 73/588
[58] Field of Search ....................... 73/12, 79, 82, 582, 73/588, 150 A

[56] References Cited

U.S. PATENT DOCUMENTS

| | | | |
|---|---|---|---|
| 2,605,633 | 8/1952 | Gow | 73/588 X |
| 2,664,743 | 1/1954 | Schmidt | 73/79 |
| 3,762,496 | 10/1973 | Milberger et al. | 73/588 |
| 3,879,982 | 4/1975 | Schmidt | 73/12 |
| 4,289,023 | 9/1981 | Rader | 73/588 X |
| 4,422,320 | 12/1983 | Moorby et al. | 73/12 |

*Primary Examiner*—Charles A. Ruehl
*Assistant Examiner*—Brian R. Tumm
*Attorney, Agent, or Firm*—Joseph H. Beumer; John R. Manning; Leon D. Wofford, Jr.

[57] ABSTRACT

An electro-mechanical impacting device (10) for testing the bonding of foam insulation (22) to metal (26). The device lightly impacts foam insulation (22) attached to metal (26) to determine whether the insulation (22) is properly bonded to the metal (26) and to determine the quality of the bond. A force measuring device, preferably a load cell (12) mounted on the impacting device, measures the force of the impact and the duration of the time the hammer head (16) is actually in contact with the insulation (22). This information is transmitted as an electric signal (20) to other elements of the invention's associated system (not part of this invention) which are capable of conditioning the signal and evaluating it electronically in order to provide a visual display on a video screen. This allows an operator to make decisions relating to bonding and the quality of bonding. The impactor (10) is designed in the form of a handgun having a driving spring (32) which can propel a plunger (14) forward to cause a hammer head (16) to impact the insulation (22). A load cell (12) is mounted on the plunger (14). A conditioning spring (48) slows down the plunger (14) just after it impacts the insulation (22) and prevents bouncing or more than one impact. The device utilizes a trigger mechanism which provides precise adjustments, allowing fireproof operation. Two types of gauges (72 and 92) project from the front of the device to provide stability, uniformity, and accuracy to the operation of the device.

27 Claims, 4 Drawing Figures

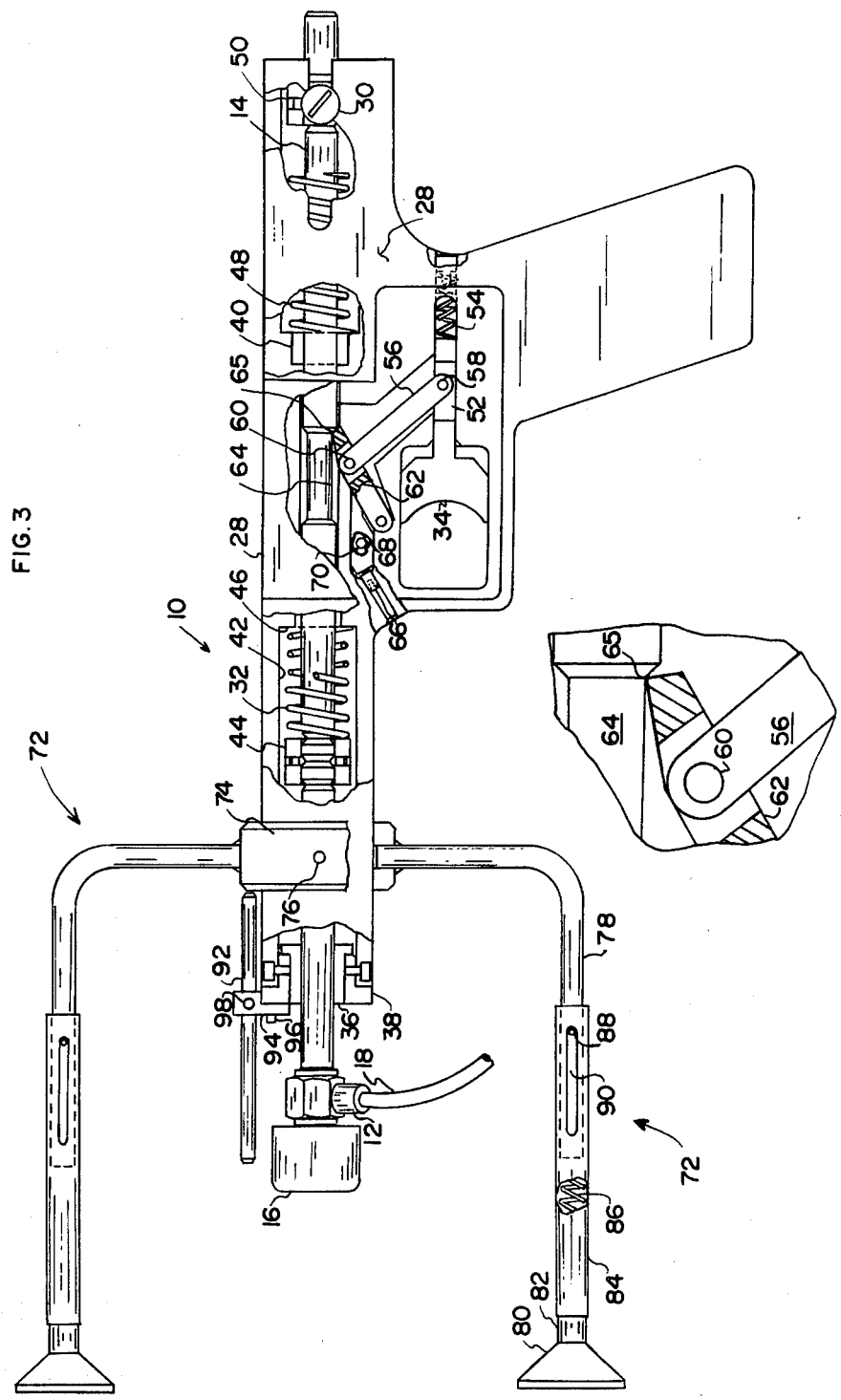

IMPACTING DEVICE FOR TESTING INSULATION

DESCRIPTION

1. Origin of the Invention

The invention described herein was made by an employee of the United States government and may be manufactured and used by or for the government of the United States of America for governmental purposes without the payment of any royalties thereon or therefor.

2. Technical Field

The present invention relates generally to nondestructive testing, and more particularly to an apparatus for testing the bonding of foam insulation attached to metal. Specifically, the invention is a device for impacting foam insulation sprayed on metal cryogenic fuel tanks in order to generate a signal which indicates the quality of the bonding of the foam insulation to the metal tanks.

3. Background of the Invention

Since the advent of the space age, which began after the World War II era, the use of liquid fuel rocket engines has become commonplace. These engines use cryogenic fuel, such as liquid oxygen and liquid hydrogen. Because of the very low temperatures of these fuels in the liquid state, insulated fuel tanks were needed. The application of sprayed-on foam insulation has proved to be the cheapest and best way to put the required insulation on the tanks. Sometimes, however, this foam insulation does not adhere well to the metal fuel tanks. Therefore, these debonded areas must be detected and repaired so that they will not cause problems connected with the firing and use of the high altitude rockets.

At the present time, the National Aeronautics and Space Administration has a requirement for a test system to evaluate the bonding of the insulation on the external tank for the Space Shuttle. The required testing system should: (1) be able to detect debonded areas consistent with the current quality control criteria for the external tank, (2) be nondestructive in nature, (3) include or be compatible with a method of verifying debonded areas, (4) be of a nature which could easily be used on a space vehicle, (5) have an output signal which could easily be interpreted by a technician, (6) have an output signal that could be permanently recorded, and (7) be able to test a substantial number of points in a large area in a short time. As part of the test system of the present invention, a device was needed to impact the foam insulation and, together with a sensing device attached to the impacting device, generate an electrical signal which would be useful in evaluating the condition of the bonding.

U.S. Pat. No. 3,653,373 to Batterman discloses an apparatus for acoustically determining periodontal health. Batterman teaches the impacting of a tooth with an impacting device and positioning a microphone on the opposite side of the tooth in order to pick up vibrations from the tooth in the form of sound waves. Specifically, it is sound waves having the resonant frequency of the tooth which are picked up. This resonant frequency then gives an indication of whether or not the tooth is solidly rooted in its socket.

U.S. Pat. No. 3,967,498 to Pezzillo discloses a tire defect detector. The Pezzillo device has a roller with an attached handle. Inside the roller is a sound generating device comprising a hammer which hits an anvil. In operation, the Pezzillo device is placed inside a tire casing and sound is generated. The echo or return resonant signal is picked up by a microphone, and the audio signal is changed into an electrical signal. The electrical signal is then compared to a predetermined scale in order to provide an indication as to whether the tire casing is sound.

Another prior art patent is U.S. Pat. No. 3,106,838 to Crooks, which discloses a system for testing a welded joint between two pieces of metal. The Crooks device continuously impacts one of the metal pieces with an electric hammer at a frequency of two to eight times per second. A probe having an attached crystal is used to detect vibrations in the other piece of metal and change these vibrations to an electric current. This current is fed directly to an oscilloscope and displayed to either (1) as a smooth and gradually decaying waveform (which indicates a good weld), or (2) a pulsating and decaying waveform (which indicates a poor weld). In the former case, the workpiece vibrates at one frequency, indicating it is one piece the size of the complete welded object. In the latter case, the two pieces tend to vibrate at different frequencies, the two signals having varying phase relationships so that they will tend to interfere with each other, amplifying in some instances and dampening the vibrations in others.

All the inventions disclosed in the above-mentioned prior art patents have at least some utility as nondestructive test devices. However, none of the prior art patents disclose a device which could accomplish the purpose which is required of the present invention. These prior art devices all appear to use a resonant or "signature" frequency to determine the condition of the workpiece. Conversely, as will be disclosed below, the present invention does not use a resonant frequency but instead uses only frequency data which is sensed while the impact to the workpiece is actually taking place. Moreover, the present invention does not use a microphone to sense resonant sound waves as does Batterman and Pezzillo.

Therefore, the object of this invention is to provide an impacting device for a non-destructive insulation bond test system which would operate on one side of the workpiece only to locate debonded areas and also check the quality of bonds in bonded or partially bonded areas. A further object is that the impacting device which tests the workpiece be portable but still provide speed and an accurate output to its related system which ultimately allows a simple decision making process and reliable results.

SUMMARY OF THE INVENTION

The present invention is a device for nondestructive testing of foam insulation attached to metal. The device comprises a housing, plunger means movably mounted within said housing and extending therefrom for impacting the insulation, said plunger means arranged to be pulled backward and held in a cocked position, a force measuring means attached to said plunger, a hammer head attached to said plunger, driving means for propelling said plunger means forward, and trigger means for releasing said plunger means from its cocked position.

BRIEF DESCRIPTION OF THE DRAWINGS

A presently preferred embodiment of the invention will now be described in detail in connection with the accompanying drawings, wherein:

FIG. 3 is an assembly drawing of the invention shown partially in section and with the housing partially cut away in order to show the parts.

FIG. 4 is an enlarged cut-away view showing how the sear holds the plunger in its cocked position.

DETAILED DESCRIPTION OF THE INVENTION

Figure 1:
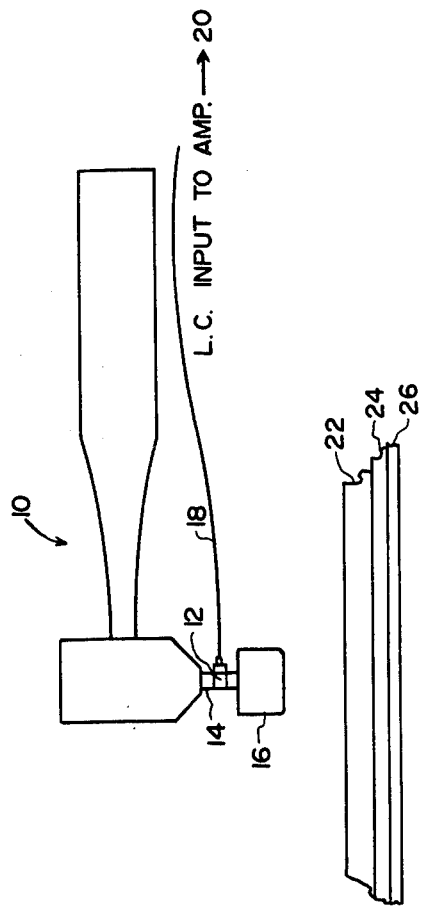
FIG. 1 is a schematic diagram of the invention in position to impact insulation in order to obtain basic data.

FIG. 1 is a schematic diagram of a preferred embodiment of the present invention. The basic equipment used in the prototype system to obtain the data needed to evaluate the bond between insulation and a metal cryogenic fuel tank is shown. The system involves the use of an impacter or lightweight hammer, shown generally at 10, which has a calibrated load cell 12 mounted on the tip of a moving rod or plunger 14. The load cell used in the prototype device is a PCB Model 208A03, which is commercially available from Piezotronics, Inc. The power supply for the load cell is PCB Model 480D06. A hammer head 16 is mounted at the end of plunger 14. Connector 18 carries force measurement data 20 from load cell 12 to other elements of the system for processing and use in evaluating the quality of bonding of the insulation, as will be described hereinbelow.

As can be seen in FIG. 1, lightweight hammer 10 is poised, ready to impact a layer of sprayed-on foam insulation 22. Insulation 22 is attached to a layer of an ablating material 24, which in turn is attached to a metal substrate 26. This metal substrate, in this instance, is the wall of an aluminum alloy fuel tank (the external tank of the Space Shuttle). The ablating material is applied under the foam to the front and back ends of the external tank and to other areas where aerodynamic heating is most severe during flight. The ablating material is designed to char away during flight, taking heat with it, thus preventing heat transfer to the cryogenic fuel in the tanks.

As indicated above, one of the basic concepts of this invention involves the use of an impacting device 10 to apply a very low force impact to the insulation. Load cell 12 measures the force and duration of the impact and transmits this data 20 to remote equipment where it may be read out as a single pulse. The period of time during which the impact is being applied to the insulation is called the forced vibration period. Normally, this period is in the range of 5 to 12 milliseconds in duration. The load cell senses only during this period so that, after the force is removed, there is no further signal on the load cell. The signal generated by the load cell is a direct and instantaneous measure of the local stiffness of the material at the point of impact. If the insulation is well bonded to the metal substrate, the stiffness or impedance will be much higher, causing a shorter duration pulse.

Figure 2:
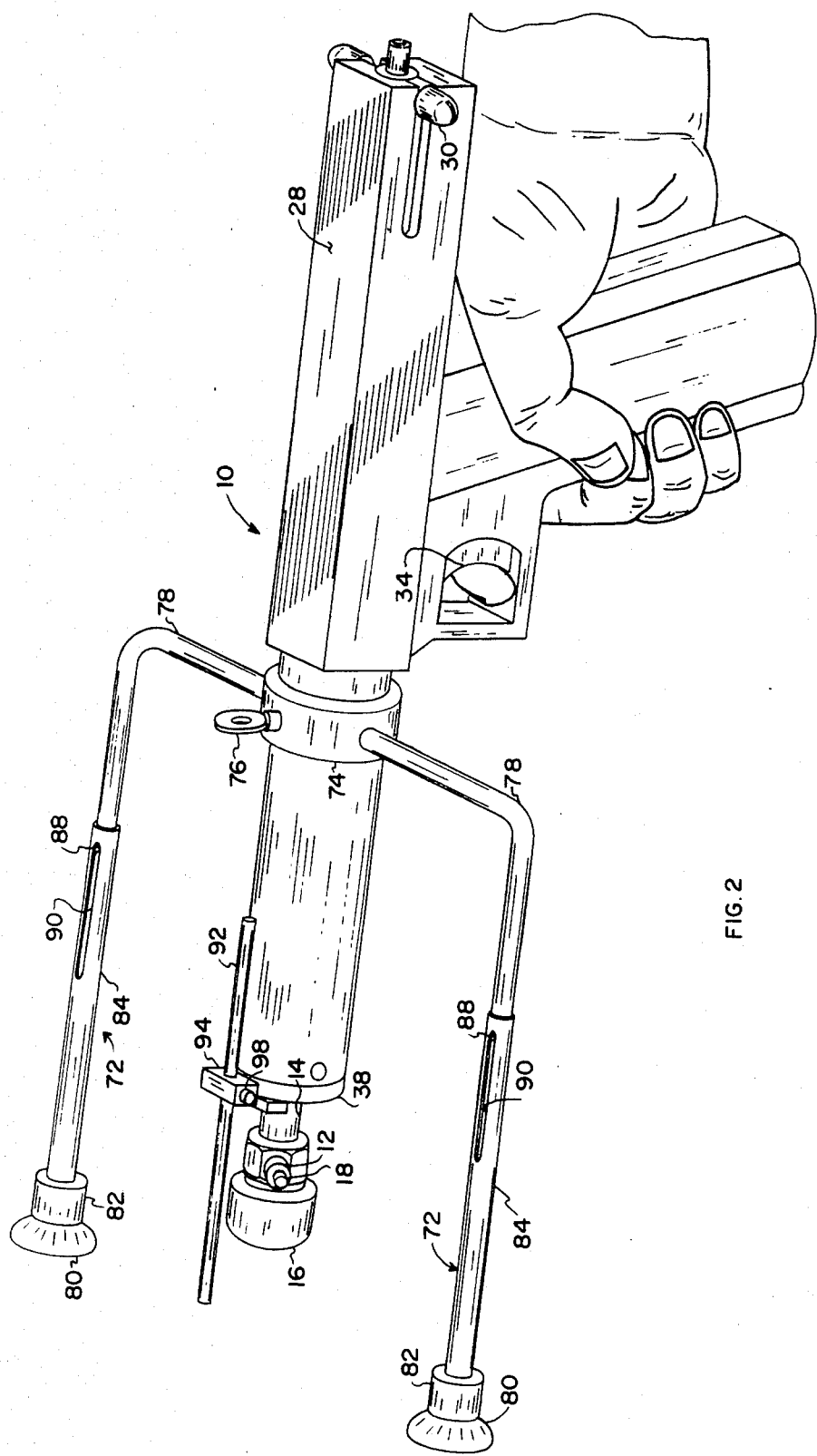
FIG. 2 is a perspective view of the invention.

FIG. 2 is a perspective view of impacting device 10 being held in the hand of an operator to demonstrate the size of the preferred embodiment.

FIG. 3 shows an assembly drawing of the preferred embodiment of impacter 10, with part of the device in section and with part of case 28 cut away in order to show the arrangement of the parts. Case 28 is designed to be approximately the same size and shape as the U.S. Army 0.45-caliber automatic pistol. Plunger 14 is a one-piece, long metal rod which extends completely through the upper part of case 28 and protrudes from both the front and back ends of case 28. Plunger 14 may be cocked by grasping the two guides 30 located at the rear end of plunger 14 and pulling plunger 14 to the rear, thus compressing the front or driving spring 32. When plunger 14 is released by trigger 34, driving spring 32 drives plunger 14 forward so that it may perform its impacting function.

Plunger 14 is supported in case 28 by a forward bushing 36 mounted in end fitting 38 and by rear bushing 40 located directly above the handle. Load cell 12 is attached to the front end of plunger 14. Hammer head 16 is attached to the front end of load cell 12. Hammer head 16, which preferably is made of an epoxy fiberglass, may be formed with a flat front impacting surface, as shown in FIG. 3. Preferably, however, the front impacting surface of hammer head 16 is slightly rounded so that the lightweight hammer will deliver uniform impacting blows even if the impacter is canted at a slight angle to the workpiece.

The front or driving spring 32 is mounted in a circular driving spring recess 42 located in the rear end of the barrel area of impacter 10. Driving spring 32 is retained under compression by front spring stop 44 and by the rear surface 46 of the barrel area. The front spring 32 may be provided in several wire diameters, giving several different spring rates, as desired.

Rear spring 48 surrounds plunger 14 in the upper rear section of the case. Rear spring 48 provides a cushioning effect when the front spring drives the plunger forward. As plunger 14 travels forward under the driving force of front spring 32, rear spring 48 is compressed, thereby slowing the plunger down immediately after the hammer head impacts the workpiece and prevents hammer head 16 from bouncing or impacting the insulation more than once. Spring 48 is retained between rear bushing 40, which also acts as a forward stop for spring 48, and by stop 50 which is attached to the rear end of plunger 14. As plunger 14 goes forward, stop 50 contacts spring 48 and compresses it, thus providing the aforementioned cushioning effect.

Impacter 10 has a precisely adjustable trigger mechanism. When trigger 34 is pulled to the rear, trigger projection 52 contacts trigger spring 54 and compresses it. At the same time, trigger projection 52 takes the lower end of trigger link 56 to the rear with it. Trigger link 56 is pivotally connected by upper trigger link pin 60 to sear 62. A pull on trigger link 56 exerts a downward pull on sear 62 and causes the tip of sear 62 to come out of machined notch 65 at the rear end of machined step 64 in plunger 14.

The trigger mechanism has a very precise adjustment. When set screw 66 is turned inward, the forward end of sear adjuster 68 is caused to move upward and sear adjuster 68 rotates about pin 70. This causes the rear end of sear adjuster 68 to push downward on sear 62, thus adjusting the precise point where the tip of sear 62 contacts the rear end of machined step 64 in plunger 14. Preferably, the tip of sear 62 will be seated in notch 65. This provides a very precise adjustment on both trigger pull and the operation of the trigger mechanism.

To provide stability to impacting device 10 during the time when the device is impacting the insulation, location guide assembly 72 is attached to the front end of the barrel area. Sleeve 74 fits over the outside of the barrel and is fastened to the barrel by two set screws 76. Extending straight out from circular sleeve 74 are two location guide rods 78. These location guide rods 78 extend out from circular sleeve 74 about three to four inches on the prototype device and are then bent forward at a 90° angle. Bumper 80 is attached to bumper rod 82, which is slidably attached to each of the two location guide rods 78. Guide rod sleeve 84 holds each of the two bumper rods 82 on its respective guide rod 78. Each guide rod sleeve 84 is attached to its respective guide rod 78 by a pin 88 attached to guide rod 78. Each pin 88 rides in a slot 90 in each guide rod sleeve 84. When impacter 10 is pushed against a workpiece, bumpers 80 contact the workpiece first and cause bumper rods 82 to compress guide rod springs 86. As will be apparent from the above discussion of the design of the location guide assembly, sleeve 74 may be oriented so that location guide rods 78 are either at the sides of the barrel area or above and below it, whichever may be desired by the operator.

An additional gauge on impacter 10 is provided by gauge rod 92 which is mounted at the end of the barrel area. Rod 92 is attached to end fitting 38 by bracket 94 and studs 96. Rod 92 may be slid forward and backward by adjusting set screw 98. This provides a way of limiting the travel of plunger 14, as may be desired by the operator or required by the type of insulation being tested.

FIG. 4 is an enlarged cut-away view of the relationship between sear 62 and plunger 14 and shows how the sear holds the plunger in its cocked position.

In operation, impacter 10 is cocked and pushed toward the workpiece by the operator until bumpers 80 contact the workpiece. Guide rod springs 86 are compressed slightly to provide a "feel" to the operator of the impacter, while maintaining very slight pressure against the workpiece. The operator takes care to insure that hammer head 16 is directly over the point to be tested and the impacter is perpendicular to the workpiece. The trigger is pulled, allowing the hammer head to hit the insulation. The impacter may then be cocked again and moved into position for the next point of impact. In practice, the device is used to test a large number of points in succession, using a matrix and following a set procedure. Impact points in the matrix are tested in a particularly prearranged order and following a particular pattern. A computer which is part of the system associated with impacter 10 keeps a record of the test results for each impact point on the insulation according to its coordinates in the matrix. When the testing is complete, the computer can map the tested area and indicate bonded and debonded areas.

The present invention has been specifically described for purposes of illustration as being used in testing portions of the exterior walls of the external tank of the Space Shuttle, consisting of curved metal plates having a foam composite sprayed on them. However, it is obvious that the invention also finds utility in the testing of panels composed of a wide variety of other kinds of materials. It is also obvious that the invention may be used for types of non-destructive testing other than the testing of panels.

The nature and scope of the present invention having been indicated and the preferred embodiment of the invention having been specifically described, what is claimed is:

1. A device for impacting insulation bonded to metal in order to test the integrity of the bond comprising:
   a housing;
   a plunger movably mounted within said housing and extending therefrom for impacting the insulation, said plunger arranged to be pulled backward and held in a cocked position;
   a force measuring means attached to said plunger;
   a hammer attached to said force measuring means;
   driving means for propelling said plunger forward; and
   trigger means for releasing said plunger from its cocked position;
   whereby said hammer impacts said insulation and said force measuring means measures both the force of the impact and the time duration of the impact and generates an electrical signal representative of both said force and said time duration.

2. The device of claim 1 wherein said force measuring means is a load cell.

3. The device of claim 1 wherein said driving means is a coil spring surrounding part of said plunger in the front part of said housing.

4. The device of claim 1 wherein said force measuring means is attached to the forward end of said plunger, and said hammer is attached to the forward end of said force measuring means.

5. The device of claim 1 comprising a cushioning means for preventing said hammer from impacting the insulation more than once when said plunger is released from its cocked position.

6. The device of claim 5 wherein said cushioning means is a coil spring surrounding part of said plunger in the rear part of said housing.

7. The device of claim 1 wherein said plunger has a machined step and a notch at the rear of said machined step for holding said plunger in its cocked position.

8. The device of claim 7 wherein said trigger means comprises:
   a trigger having a rearwardly extending shaft;
   a trigger spring mounted behind said trigger shaft for biasing said trigger forward;
   a trigger link pivotally attached to said trigger; and
   a sear pivotally attached to said trigger link and having one end pivotally attached to said housing, whereby said sear may project into said notch in said plunger and hold said plunger in the cocked position.

9. The device of claim 1 comprising a location guide assembly attached to said housing, said location guide assembly having two L-shaped location guide rods extending straight out from said housing and then forward at a 90° angle.

10. The device of claim 9 comprising two sleeves, one end of each said sleeve being slidably attached to one of said location guide rods.

11. The device of claim 10 comprising two spring-loaded bumper rods, each said bumper rod being slidably attached to the opposite end of one of said sleeves.

12. The device of claim 11 wherein each said spring-loaded bumper rod has an attached bumper made of a resilient material.

13. The device of claim 1 wherein said housing has two slots near the rear end of said housing, said slots being located on opposite sides of said housing.

14. The device of claim 13 comprising two guides mounted on opposite sides of said plunger, said guides extending through said slots so that said guides may travel forward in said slots when said plunger is released from its cocked position.

15. The device of claim 1 comprising a rod which is slidably attached to the front end of said case and arranged so that the distance it projects forward of the end of said case is adjustable, for limiting the forward travel of said plunger.

16. The device of claim 1 wherein the front surface of said hammer is slightly rounded for delivering uniform impacting blows even if the device is canted.

17. The device of claim 2 wherein said load cell is attached to the forward end of said plunger, and said hammer is attached to the forward end of said load cell.

18. The device of claim 17 comprising a cushioning means for preventing said hammer from impacting the insulation more than once when said plunger is released from its cocked position.

19. The device of claim 18 wherein said plunger has a machined step and a notch at the rear of said machined step for holding said plunger in its cocked position.

20. The device of claim 19 wherein said trigger means comprises:
   a trigger having a rearwardly extending shaft;
   a trigger spring mounted behind said trigger shaft for biasing said trigger forward;
   a trigger link pivotally attached to said trigger; and
   a sear pivotally attached to said trigger link and having one end pivotally attached to said housing, whereby said sear may project into said notch in said plunger and hold said plunger in the cocked position.

21. The device of claim 20 comprising a location guide assembly attached to said housing, said location guide assembly having two L-shaped location guide rods extending straight out from aid housing and then forward at a 90° angle.

22. The device of claim 21 comprising two sleeves, one end of each said sleeve being slidably attached to one of said location guide rods.

23. The device of claim 22 comprising two spring-loaded bumper rods, each said bumper rod being slidably attached to the opposite end of one of said sleeves.

24. The device of claim 23 wherein each said spring-loaded bumper rod has an attached bumper made of a resilient material.

25. The device of claim 24 wherein said housing has two slots near the rear end of said housing, said slots being located on opposite sides of said housing.

26. The device of claim 25 comprising two guides mounted on opposite sides of said plunger, said guides extending through said slots so that said guides may travel forward in said slots when said plunger is released from its cocked position.

27. The device of claim 26 wherein the front surface of said hammer is slightly rounded for delivering uniform impacting blows even if the device is canted.

* * * * *